United States Patent [19]

Tarver

[11] Patent Number: 5,012,821
[45] Date of Patent: May 7, 1991

[54] MEDICAL RESTRAINT APPARATUS

[76] Inventor: Charles W. Tarver, 4058 Sequoyah Ave., Knoxville, Tenn. 37919

[21] Appl. No.: 348,768

[22] Filed: May 8, 1989

Related U.S. Application Data

[63] Continuation-in-part of Ser. No. 193,668, May 23, 1988, abandoned.

[51] Int. Cl.⁵ .............................................. A61F 5/37
[52] U.S. Cl. ..................................... 128/876; 128/879
[58] Field of Search ............................. 128/869–876, 128/87 C, 80 R, 80 A, 87 A, 87 B, DIG. 15, 882; 5/495

[56] References Cited

U.S. PATENT DOCUMENTS

| | | | |
|---|---|---|---|
| 794,457 | 7/1905 | Gaiter | 128/876 |
| 1,887,022 | 11/1932 | Hoffman | 128/877 |
| 1,969,314 | 8/1934 | Millett | 128/876 |
| 2,215,454 | 9/1940 | Condit | 128/870 |
| 2,245,293 | 6/1941 | Ogburn | 128/882 |
| 2,295,806 | 9/1942 | Peterson | 128/878 |
| 2,425,489 | 8/1947 | Peterson | 128/876 |
| 2,697,436 | 12/1954 | Coston | 128/877 |
| 2,706,477 | 4/1955 | Daake | 128/872 |
| 2,848,993 | 8/1958 | Terrell | 128/876 |
| 2,991,785 | 7/1961 | Terrell | 128/876 |
| 3,042,031 | 7/1962 | Reed | 128/876 |
| 3,474,781 | 10/1969 | Gaylord, Jr. | 128/876 |
| 3,878,844 | 4/1975 | Tobias | 128/876 |
| 4,172,453 | 10/1979 | Leckie | 128/878 |

Primary Examiner—Robert A. Hafer
Assistant Examiner—Michael Brown

[57] ABSTRACT

A medical restraint apparatus (10) for use in securing a patient to a bed is provided. The apparatus (10) includes a web strap (12) which extends across the width of the bed and secured at its opposite ends to the bed frame. A pair of cuffs (20, 20') are mounted on the web strap (12) at spaced locations such that the patient's wrists will be held at his side. The cuffs (20, 20') are releasably secured on the web strap (12) at selected locations (58A, 58B) and the effective spacing between the locations at which the cuffs (20, 20') are mounted on the strap can be adjusted to accommodate patients of different sizes.

13 Claims, 3 Drawing Sheets

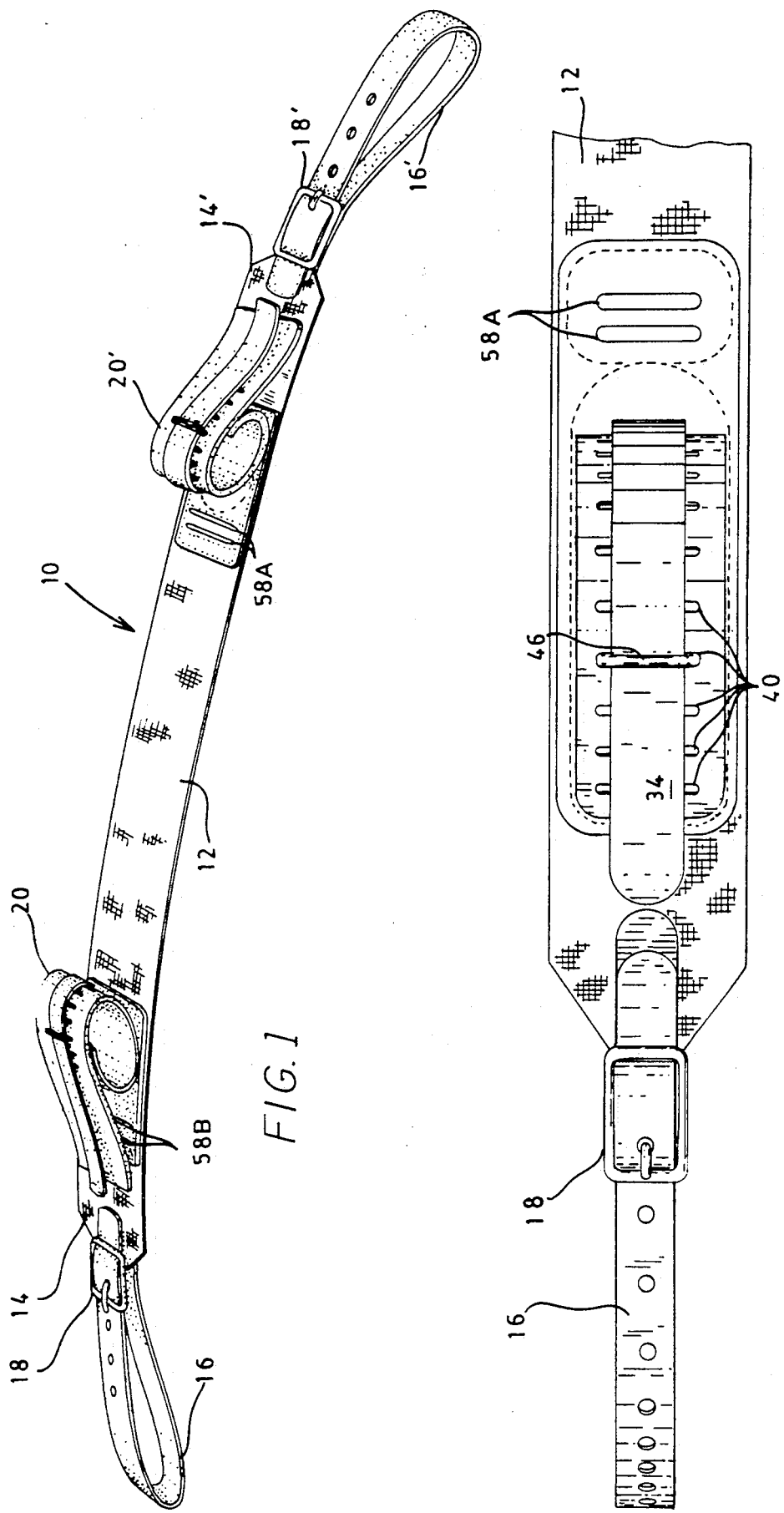

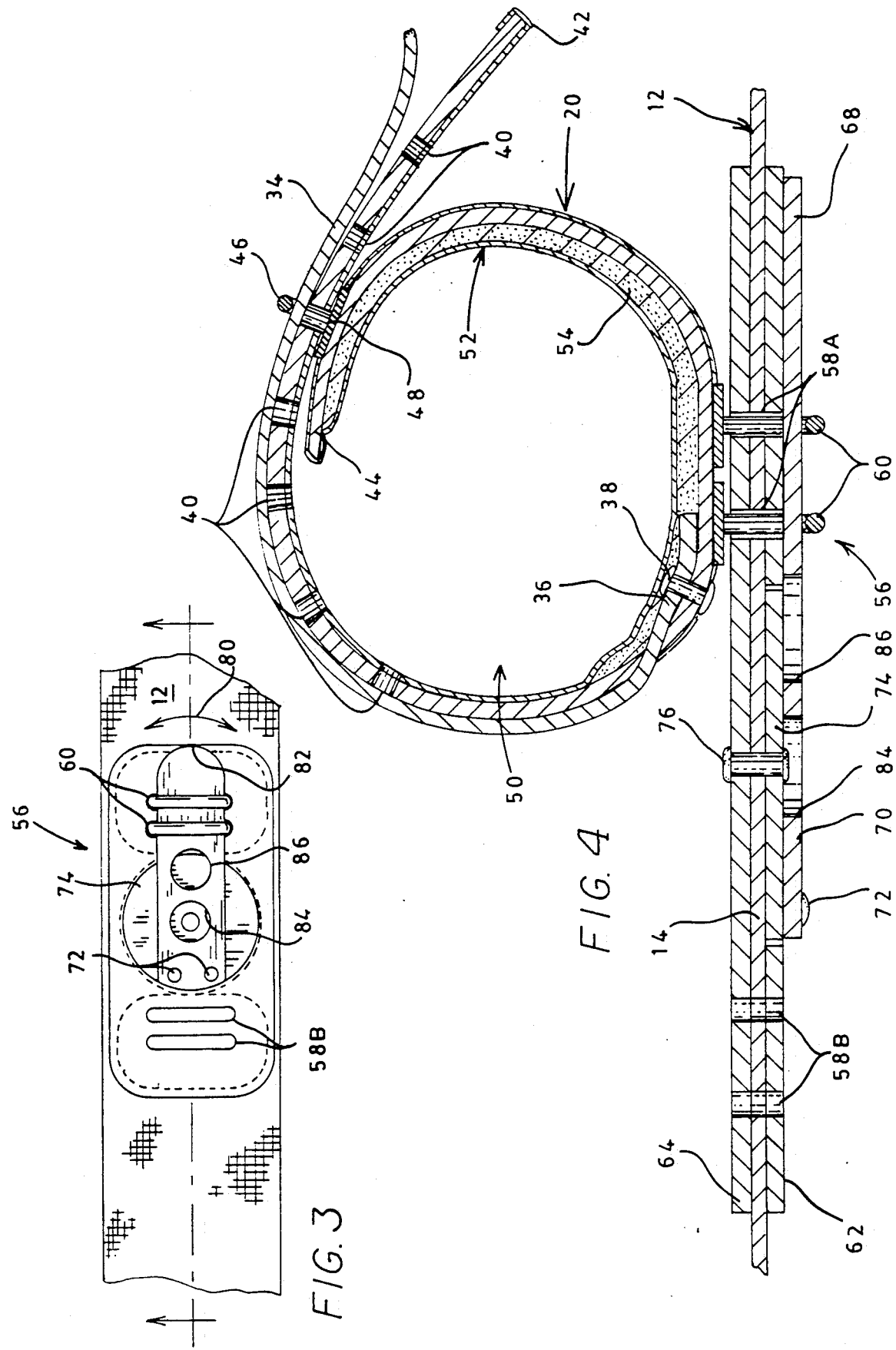

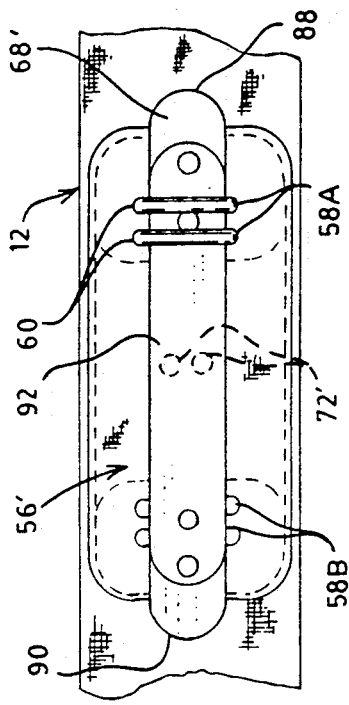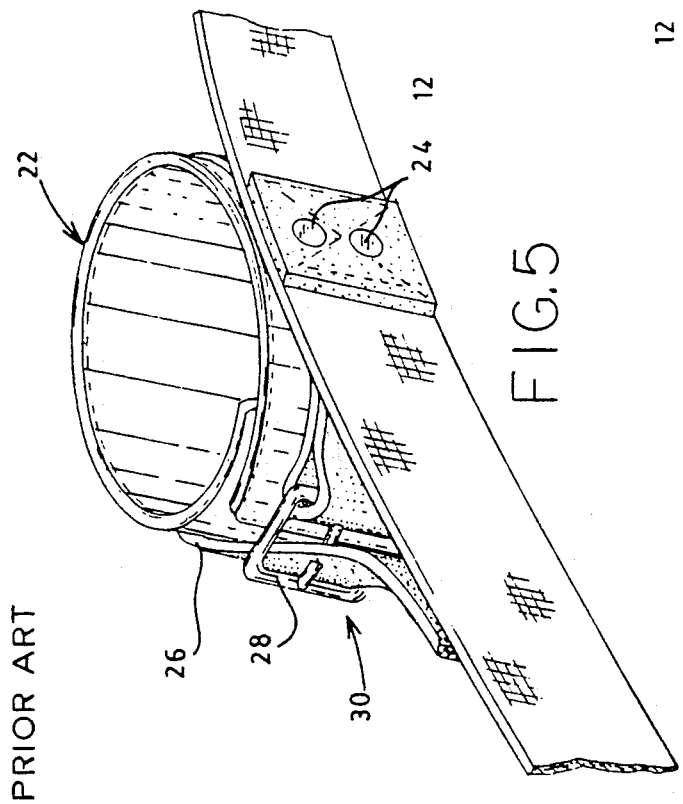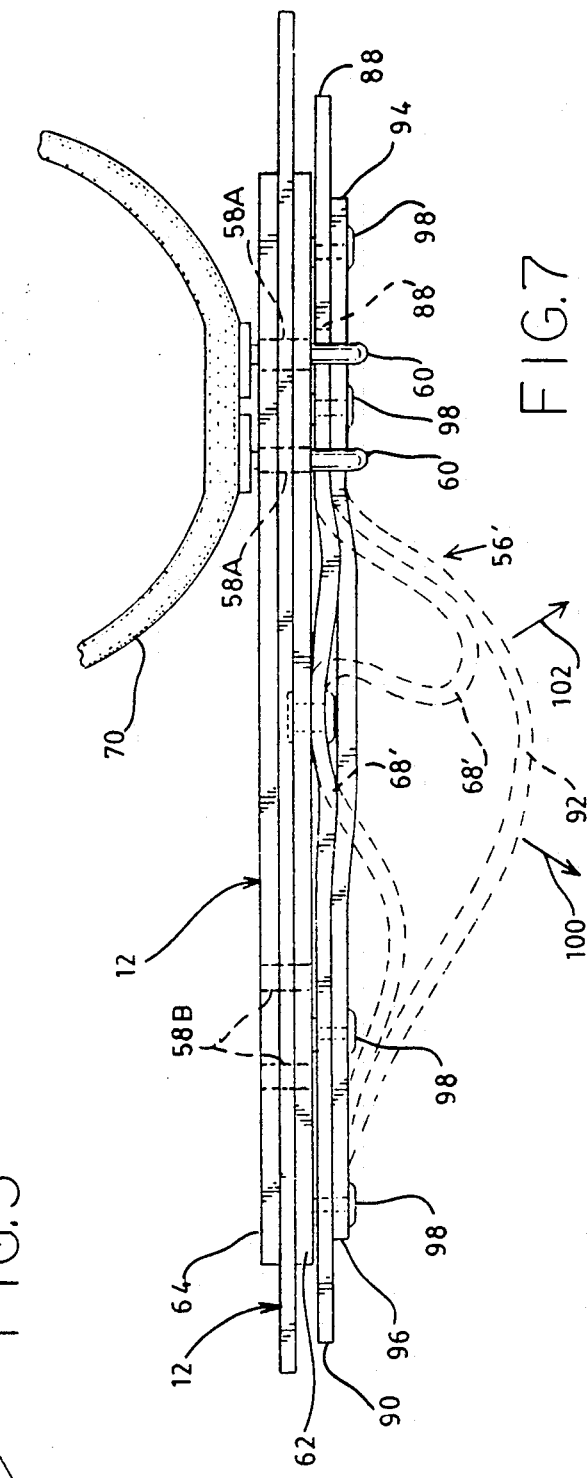

5,012,821

MEDICAL RESTRAINT APPARATUS

This is a continuation-in-part application based upon parent application Ser. No. 193,668 filed May 23, 1988, now abandoned.

TECHNICAL FIELD

This invention relates to a medical restraint apparatus, and more specifically concerns such an apparatus for securing the limbs of a patient to a bed.

BACKGROUND ART

Medical restraint apparatuses used for securing a patient to a bed have heretofore been known. Such apparatuses commonly include a web strap which can be secured at its opposite ends to the frame of a bed. The strap is provided with a pair of spaced cuffs fixedly secured at spaced locations to the web strap. These cuffs serve to patient to a bed and restrain the patient in a prone position.

Prior art medical restraint apparatuses come in various sizes. In the devices used for small sixteen inches. For larger sized patients, the spacing is usually twenty-four inches. Moreover, with the cuffs fixedly secured to the web strap, damage to a cuff requires replacement of the medical restraint apparatus eventhough the other cuff and/or the web strap are in good condition.

Known prior art devices use a buckle and strap closure for the cuff. While this closure is effective in firmly securing the cuff to the limb of a patient, it is awkward and difficult to manipulate, especially if a patient is resisting application of the medical restraint apparatus to his limbs. Certain of these prior art restraining devices are disclosed in U.S. Pat. Nos. 4,172,453; 3,878,844; 3,474,781; 3,042,031; 2,991,785; 2,848,993; 2,697,436; 2,425,489; 2,295,806; 1,969,314 and 1,887,022. However, none of these devices feature easily releasable cuffs to facilitate replacement or adjustments to the position of the cuffs, and in general they are difficult to manipulate.

Accordingly, it is an object of the present invention to provide an improved medical restraint apparatus for restraining a patient to a bed and in which the cuffs are removable such that a damaged cuff can be replaced.

Another object of the present invention is to provide such a medical restraint apparatus in which the effective spacing between the cuffs can be adjusted along the length of the web strap to accommodate patients of various sizes.

It is yet another object of the present invention to provide such a medical restraint apparatus having an improved cuff closure which can be readily manipulated by a nurse or other medical personnel to simplify application of the cuffs to the wrist or ankles of a patient to be restrained.

Other objects and advantages of the medical restraint apparatus constructed in accordance with various features of the present invention will become apparent upon reading the detailed description together with the drawings described as follows.

DISCLOSURE OF THE INVENTION

In accordance with various features of the present invention, an improved medical restraint apparatus for securing a patient to a bed is provided. The apparatus includes a web strap having opposite ends which can be secured to a bed frame. A pair of cuffs are mounted on the web strap at spaced locations. In this connection, securing means are provided for releasably securing the cuffs to the web strap such that the effective spacing between the locations at which the cuffs are mounted on the web strap can be adjusted to accommodate patients of various sizes. Moreover, the cuffs can be replaced if they are damaged without the need for discarding the cooperating cuff and the web strap.

BRIEF DESCRIPTION OF THE DRAWINGS

FIG. 1 illustrates a medical apparatus constructed in accordance with various features of the present invention. This apparatus has at selected locations along the length of the web strap such that the spacing between the cuffs can adjusted.

FIG. 2 illustrates the closure for a cuff, together with a cinch strap for securing one end portion of the web strap to the bed. In this view, a portion of the apparatus is broken away.

FIG. 3 illustrates securing means for releasably securing the cuff to the web strap at selected locations. FIG. 3 illustrates a portion of the securing means which rests upon the bed, and portions of the apparatus are broken away as illustrated.

FIG. 4 illustrates a sectional side elevation view of a single cuff and the securing means for mounting the cuff on the web strap. This view is taken along line 3—3 in FIG. 3.

FIG. 5 illustrates a typical prior art cuff, together with the securing means for fixedly securing the cuff to the web strap and a typical buckle and strap closure for the cuff.

FIG. 6 illustrates a rear view of alternate securing means for releasably securing the cuffs of the medical restraint apparatus of the present invention.

FIG. 7 illustrates a partial side elevation of a medical restraint apparatus of the present invention depicting alternate means for releasably securing the cuffs of the present invention.

BEST MODE FOR CARRYING OUT THE INVENTION

Referring now to the drawings, a medical restraint apparatus is generally indicated at 10 in the figures. The medical restraint apparatus of the present invention comprises an elongated web strap 12. This strap 12 is conventionally about three inches wide and about forty inches long. However, it will be recognized that these dimensions can vary depending on the size of the bed to which a patient is secured by use of the apparatus 10. The web strap 12 is preferably fabricated from a flexible and strong material such as a suitable canvass web, leather or the like.

This web strap 12 has opposite end portions 14 and 14' as illustrated in FIG. 1. These end portions each carry a cinch strap 16 and 16', respectively. It will be noted in the depicted embodiments that the cinch straps 16 an 16' are provided with a conventional buckle which serves as a closure for securing the opposite end portions of the strap to the frame of a bed at its opposite sides. For example, cinch strap 16 is secured to the elongated frame member of a bed on one side thereof, and cinch strap 16' is secured to the elongated frame member on the opposite side of the bed frame. The buckles 18 and 18' serve to fix and cinch the web strap 12 against the mattress.

In a medical restraint apparatus of the type shown in FIG. 1, the apparatus is mounted onto the bed such that the web strap 12 is about hip high on the mattress, i.e., the patient's hips rest on the web strap 12. This position is used when it is desired to secure the wrists of the patient. Obviously, the medical restraint apparatus would be placed proximate the feet of the patient and secured to the frame at such location when it is desired to use the apparatus for securing the patient's ankles. A pair of cuffs 20 and 20' are mounted at spaced locations on the web strap 12 as is shown in FIG. 1.

A prior art cuff is depicted in FIG. 5. As illustrated, this prior art cuff 22 is secured fixedly to the web strap 12 by use of suitable rivets 24 as shown in FIG. 5. The cuffs mounted at spaced locations on the prior art device, shown partially in FIG. 5, and this spacing cannot be adjusted since the cuffs are fixedly secured to the web strap 12. Thus, if a prior art cuff is damaged and rendered useless, the entire medical restraint apparatus must be discarded.

Closure of the prior art cuff 22 is accomplished by a suitable strap 26 and buckle 28 shown in FIG. 5. This type of closure, which is generally indicated at 30, is difficult to manipulate by medical personnel attempting to restrain a patient to a bed by placing the patient's limb within the cuff 22.

In the improved medical restraint apparatus shown at 10 in FIGS. 1-4, each improved cuff 20 and 20' is provided with an improved closure which enhances the ease with which the cuff can be secured to the patient's limb proximate the ankle or wrist. In this regard, the improved closure includes a closure strap 34 which is secured at end portion 36 to the cuff 20 by a suitable rivet 38 (see FIG. 4). Openings generally indicated at 40 are spaced along the length of the cuff proximate end portion 42 thereof. The opposite end portion 44 of the cuff 20 is provided with a suitable staple 46. This staple is secured at one end portion 48 to end portion 44 of a cuff and defines an opening between the cuff surface and the staple cross member through which the end portion 36 of the closure strap 34 can be extended. Thus, in order to close the cuff 20, as is shown in FIG. 4 and which is representative of the cuff 20', the patient's wrist is placed within the opening defined at 50. End portion 42 of the cuff is then pulled until it tightly engages the wrist or ankle. At this point, the staple 46 which is properly proportioned, is inserted into the selected opening 40 which provides a secure fit. The two end portions 42 and 44 of a cuff are then joined by inserting closure strap 34 through the opening defined in the staple 46. It has been found that this type of closure can be more readily operated by a medical staff member, and keeps the hands freer to deal with a recalcitrant patient.

In the preferred embodiment shown in greater detail in FIG. 4, the inside portion 52 is provided with suitable padding 54 substantially about its perimeter to protect the limb of the patient secured within the cuff 20 or 20'.

In accordance with an important feature of the present invention, the medical restraint apparatus 10 includes securing means generally indicated at 56 in FIGS. 3 and 4, which serve to releasably secure each of the cuffs 20 and 20' onto the web strap 12 at selected locations. In this connection, the securing means of the present invention allows adjusting the effective spacing between the locations at which the cuffs are mounted onto the web strap. The securing means 56 is substantially identical for each cuff 20 and 20', and accordingly, a description of one such securing means will suffice as a description of the other.

The securing means 56 includes a plurality of openings defined in the web strap 12. More specifically, referring to FIG. 4, the openings 58A are defined in the web strap 12 at a location for which it is desirable to secure the cuff 20. A further pair of openings 58B is provided on the end portion 14 of the web strap 12 at another location to which it is desirable to secure the cuff 20. Staple means generally indicated at 60 are mounted on the cuff as indicated in FIG. 4. This staple means has a configuration similar to the configuration of the staple 46 described in greater detail above. The staple means 60 are carried by the cuff and proportioned for being received through the web strap openings 58A when it is desired to secure the cuff to the strap at the locations of these openings. Further, the staple means 60 are also proportioned for being received within openings 58B when it is desired to secure the cuff at that location on the web strap 12.

In the embodiment depicted in the figures, underlaying and overlaying reinforcement members 62 and 64, respectively, are secured to the end portions of the web strap 12 to which the cuffs are secured. These reinforcement members sandwich a portion of the end portions 14 and 14' of the strap web therebetween, and are provided with suitable openings which register with the openings 58A and 58B defined in the web strap. These reinforcement members normally comprise leather, in the preferred embodiment, which is sewn to the web strap 12. Other materials can obviously be used for the reinforcement members.

A closure strap 68 has one end portion 70 which is secured to the web strap by a suitable rivet or rivets 72. In the embodiment depicted in FIG. 4, the end portion 70 of closure strap 68 is secured to the web strap 12 indirectly by first securing the end portion 70 to a rotatable member 74 which is in turn secured to the web strap 12 by rivet 76. Rotatable member 74 is circular in cross-sectional outline (see FIGS. 3 and 4). It can be rotated 360 degrees in the preferred embodiment such that the direction of the extension of the closure strap 68 can be varied in order to secure the cuff 20 at the location shown in FIGS. 3 and 4 where the staple 60 extends through openings 58A. Similarly, rotation of the closure strap 68 can be accomplished for mounting the cuff 20 at the location corresponding with the opening 58B. Thus, the closure strap 68 can be rotated in the direction of the bi-directional arrow 80 shown in FIG. 3 to adjust the location at which the cuff 20 is secured to the web strap 12 since the openings 58A and 58B are on opposite sides of the location, the closure strap is secured to the web strap. Of course, the end portion 82 of the closure strap 68 must be removed from the opening defined within the staples 60 prior to rotation of the closure strap 68 in the direction of the arrow 80.

In the embodiment shown in FIG. 3, the closure strap 68 is provided with a suitable opening 84 (also see FIG. 4) which serves to provide access through the closure strap 68 to the rivet 76. A further opening 86 (see FIG. 4) is also provided in the closure strap 68 to facilitate bending the strap as when it is made of leather. This assists in preventing cracking of the leather and adds flexibility to the strap.

Utilization of the indirect attachment of end portion 70 of closure strap 68 to the strap web 12 through the rotatable member 74 has been found to facilitate rotation of the strap 68 in a direction of arrow 80. However, it will be recognized by those skilled in the art that end portion 70 can be rotatably secured directly to the web strap 12 or the underlying reinforcement member 62 as is desired.

In FIGS. 6 and 7 an alternative securing means for releasably securing the cuffs 20 and 20' is illustrated generally at 56'. As illustrated, the securing means 56' includes a closure strap 68' which is secured to the web strap 12 between the openings 58A and 58B with suitable fastening means such as the rivets 72'. In this regard, the strap 68' is secured to the web strap 12 approximately midway its length such that the opposite end portions 88 and 90 of the closure strap 68' extend beyond the openings 58A and 58B, respectively. Accordingly, when the cuff 20 or 20' is positioned such that the staples 60 extend through the openings 58A, the end portion 88 of the closure strap 68' is inserted through the opening defined by the staples 60 to secure the cuff in position as illustrated in FIGS. 6 and 7. Similarly, when the cuff 20 or 20' is positioned such that the staples 60 extend through the openings 58B the end portion 90 of the closure strap 68' is inserted through the opening defined by the staples 60 to secure the cuff in position.

In the preferred embodiment of the securing means 56' the closure strap 68' is provided with a pull strap 92 to facilitate the removal of the closure strap 68' from the staples 60 and insertion of the strap 68' into the staples 60. As best illustrated in FIG. 7, the pull strap 92 defines opposite end portions 94 and 96 which are secured to the closure strap 68' proximate the opposite end portions 88 and 90, respectively, with suitable fasteners such as the rivets 98. It will be noted that the central portion of the pull strap 92 is not secured to the closure strap 68' so as to allow ones fingers to be inserted between the closure strap 68' and the pull strap 92, and, thus, to allow the grasping of the pull strap 92. Accordingly, as illustrated in FIG. 7, removal of the end portion 88, and the release of the cuff 20 or 20', can quickly and easily be accomplished by pulling outwardly on the central portion of the pull strap 92 in generally the direction of the arrow 100. It will be recognized that in doing so the end portion 94 of the pull strap 92 pulls the end portion 88 of the closure strap 68 from the staples 60. Similarly, when the staples 60 are in the openings 58B the end portion 90 of the closure strap 68' can be quickly and easily removed by pulling outwardly on the central portion of the pull strap 92 in generally the direction indicated by the arrow 102. It will also be recognized that the pull strap 92 can also be utilized to facilitate the positioning of the closure strap 68 for insertion into the staples 60 when the cuff 20 or 20' is being secured to the web strap 12.

Whereas in the preferred illustrated embodiment the staple means 60 comprises a pair of cooperating u-shaped staples which are received in a pair of registering openings, it will be recognized that the staple means 60 can comprise a single staple. However, it will be appreciated that the use of two selectively spaced staples provide for a stronger and more stable mounting of the cuffs.

From the foregoing detailed description, it will be recognized that an improved medical restraint apparatus has been provided. This apparatus includes cuffs which can be readily removed as when one cuff is damaged. This feature prevents the necessity of discarding the entire medical restraint apparatus in the event only one cuff is damaged. Thus, a replacement cuff can simply be substituted for the damaged cuff, and the useful life of the medical restraint apparatus will continue.

Another feature of the present invention, which can be observed in the figures, is the adjustability of the center-to-center spacing of the cuffs. In this regard, a single medical restraint apparatus can be used for patients having various sizes. More specifically, in the embodiment depicted, end portion 14 of the web strap 12 is provided with two locations 58A and 58B at which a cuff can be secured. Similarly, end portion 14' of the web strap 12 is provided with two locations 58A and 58B at which the cuff 20' can be secured to this end portion 14'. For ease of reference, the location defined by the placement of the openings 58A will be towards the center of the strap at each end portion 14 and 14'. The locations defined by the openings 58B will be that which is closest to the operatively associated cinch straps 16 and 16', respectively. Thus, there are three spacings between the cuffs which can be readily established by a medical restraint apparatus of the type shown in FIGS. 1 and 2. For example, when cuff 20 is secured, as shown in FIG. 1, at the location of openings 58A, and cuff 20' is secured at the location of openings 58B on the opposite ends of the strap, an intermediate spacing between cuffs 20 and 20' is established. This spacing is preferably about twenty inches from cuff center to cuff center. If cuff 20 is moved to the location of the openings 58B, then the center-to-center spacing between the cuffs is about twenty-four inches. On the other hand, if cuff 20' is moved to the location defined by openings 58A, the center to-center spacing is about sixteen inches. Thus, the medical restraint apparatus is readily adapted for various sized patients.

While a preferred embodiment has been shown and described, it will be understood that there is no intent to limit the invention by such disclosure, but rather it is intended to cover all modifications and alternate constructions falling within the spirit and scope of the invention as defined in the appended claims and the equivalents thereof.

I claim:

1. A medical restraint apparatus for the limbs of a patient, said apparatus comprising:

a web strap having first and second opposite ends which can be secured to a bed frame and having forward and rearward surfaces, said web strap defining at least a pair of cuff securing openings;

a pair of cuffs for receiving and restraining said limbs and for being releasably mounted on said forward surface of said web strap at spaced locations, each of said cuffs including closure means for releasable securing said cuffs to said limbs of said patient; and securing means for releasably securing said cuffs on said web strap whereby said cuffs can be selectively removed from said web strap for repair or replacement, said securing means including at least one staple carried by each said cuff, each said staple being substantially u-shaped and having a pair of spaced apart end portions secured to said cuff whereby said staple extends outwardly from said cuff and defines a locking aperture, each said staple being proportioned to be received through one said opening of said web strap and to extend beyond said rearward surface of said web strap, said securing means further comprising at least a pair of closure straps secured to said rearward surface of said web strap, one said closure strap being operatively associated with each said cuff, each said closure strap having a first free end portion for being slidably received through said securing aperture of said staple as said staple is received through said web strap.

2. The medical restraint apparatus of claim 1 wherein said web strap is provided with at least first and second said openings operatively associated with each said cuff for alternately receiving said staple of said cuff, whereby the effective spacing between the locations at which said cuffs are mounted on said web strap can be adjusted.

3. The medical restraint apparatus of claim 2 wherein one said closure strap is rotatably secured to said web strap at a point between said first and second openings operatively associated with one said cuff and the other said closure strap is rotatably secured to said web strap at a point between said first and second openings operatively associated with the other said cuff, whereby said closure straps can be selectively rotated such that said free end portions can engage said staples extending through said first openings or staples extending through said second openings.

4. The medical restraint apparatus of claim 2 wherein each said closure strap further includes a second free end portion, and wherein one said closure strap is secured to said web strap at a point between said first and second openings operatively associated with one said cuff and the other said closure strap is secured to said web strap at a point between said first and second openings operatively associated with the other said cuff, whereby said first end portions of said closure straps engage staples received through said first openings and said second free end portion of said closure straps engage staples received through said second openings.

5. The medical restraint apparatus of claim 4 wherein each said closure strap is provided with a pull strap having a first end portion secured to said closure strap at a point proximate said first free end portion of said closure strap, and a second end portion secured to said closure strap at a point proximate said second free end portion of said closure strap, whereby selected actuation of said pull strap facilitates the removal of said first and second free end portions of said closure strap from said staples.

6. The medical restraint apparatus of claim 1 wherein web strap defines at least one cooperating pair of said openings operatively associated with each said cuff, said openings of each said cooperating pair being selectively spaced, and wherein each said cuff is provided with a cooperating pair of said staples for being received through said cooperating pair of said openings, whereby said first free end portion of said closure strap is slidably received through said locking apertures of both said staples of said cooperating pair of staples.

7. The medical restraint apparatus of claim 6 wherein said web strap defines at least first and second cooperating pairs of said openings operatively associated with each said cuff for alternately receiving said cooperating pairs of said operatively associated cuff, whereby the effective spacing between the locations at which said cuffs are mounted on said web strap can be adjusted.

8. The medical restraint apparatus of claim 7 wherein one said closure strap is rotatably secured to said web strap at a point between said cooperating pairs of said openings operatively associated with one said cuff and the other said closure strap is rotatably secured to said web strap at a point between said cooperating pairs of said openings operatively associated with the other said cuff, whereby said closure straps can be selectively rotated such that said free end portions can selectively engage staples extending through either of said cooperating pairs of openings associated with said cuffs.

9. The medical restraint apparatus of claim 7 wherein each said closure strap further includes a second free end portion, and wherein one said closure strap is secured to said web strap at a point between said cooperating pairs of openings operatively associated with one said cuff and the other said closure strap is secured to said web strap at a point between said cooperating pairs of openings operatively associated with the other said cuff, whereby said first free end portion of said closure straps engage staples received through said first cooperating pairs of openings and said second free end portion of said closure straps engage staples received through said second cooperating pairs of said openings.

10. The medical restraint apparatus of claim 9 wherein each said closure strap is provided with a pull strap having a first end portion secured to said closure strap at a point proximate said first free end portion of said closure strap, and a second end portion secured to said closure strap at a point proximate said second free end portion of said closure strap, whereby selected actuation of said pull strap facilitates the removal of said first and second free end portion of said closure strap from said staples.

11. The medical restraint apparatus of claim 1 wherein each said cuff defines a first end portion provided with a plurality of spaced openings, and wherein said closure means for releasably securing said cuffs to said limbs includes a staple mounted proximate a second end portion of said cuff for being selectively received through one of said openings of said cuff, said staple having a pair of spaced free end portions for being secured to said cuff and defining a locking aperture, said closure means also comprising a closure strap having one end secured to said cuff and an opposite end proportioned for being received through said staple after said staple has been received within an opening in said cuff to join opposite ends of said cuffs and secure said cuff on a patient's limb.

12. A medical restraint apparatus for engaging the limbs of a patient, said apparatus comprising:
a web strap having first and second opposite ends which can be secured to a bed frame, and having forward and rearward surfaces, said web strap defining first and second cooperating pairs of openings disposed toward said first end of said web strap and third and fourth cooperative pairs of openings disposed toward said second end of said web and thereby spaced from said first and second cooperating pairs of said openings, said web strap being provided with first and second closure straps, each said closure strap having a first and second free end portion, said first closure strap being secured to said rearward surface of said web strap between said first and second cooperating pairs of openings, and said second closure strap being secured to said rearward surface of said web strap between said third and fourth cooperating pairs of openings; and
a pair of cuffs for receiving and restraining said limbs and for being releasably mounted on said forward surface of said web strap at spaced locations, each said cuff being provided with a pair of outwardly extending staples for being received through one of said cooperating pairs of openings in said web strap, each said staple having a pair of spaced free end portions secured to said cuff and defining a locking aperture receptive of one of said free end portions of said closure straps as said staple extends through one of said cooperating pairs of openings in said web strap whereby each said cuff is releasably secured to said web strap, each said cuff defining a first end portion provided with a plurality of spaced further openings, and defining a second end portion carrying a further staple for being selectively received through one of said further openings of said cuff, said staple having a pair of spaced free end portions secured to said cuff and defining a locking aperture, each said cuff also including a further closure strap having one end secured to said cuff and an opposite end proportioned for being received through said further staple after said further staple has been received within one of said further openings in said cuff to join opposite ends of said cuffs and secure said cuffs on a patient's limbs.

13. The medical restraint apparatus of claim 12 wherein each said closure strap is provided with a pull strap having a first end portion secured to said closure strap at a point proximate said first free end portion of said closure strap, and a second end portion secured to said closure strap at a point proximate said second free end portion of said closure strap, whereby selected actuation of said pull strap facilitates the removal of said first and second free end portions of said closure strap from said staples.

* * * * *